United States Patent
Bessonart

(10) Patent No.: US 6,907,931 B2
(45) Date of Patent: Jun. 21, 2005

(54) METHOD AND DEVICE FOR DRIVING INTO THE MARINE SUBSURFACE AT GREAT DEPTHS, A TUBULAR TOOL FOR SOIL SAMPLING OR FOR MEASURING SOIL CHARACTERISTICS

(76) Inventor: Julien Bessonart, 9, rue Chante Coq, F-92800 Puteaux (FR)

( * ) Notice: Subject to any disclaimer, the term of this patent is extended or adjusted under 35 U.S.C. 154(b) by 57 days.

(21) Appl. No.: 10/204,580
(22) PCT Filed: Feb. 15, 2001
(86) PCT No.: PCT/FR01/00453
§ 371 (c)(1), (2), (4) Date: Nov. 8, 2002
(87) PCT Pub. No.: WO01/61309
PCT Pub. Date: Aug. 23, 2001

(65) Prior Publication Data
US 2003/0116322 A1 Jun. 26, 2003

(30) Foreign Application Priority Data
Feb. 17, 2000 (FR) .............................. 00 01956

(51) Int. Cl.⁷ ................................................ E21B 7/26
(52) U.S. Cl. ............................ 166/336; 175/20; 175/58
(58) Field of Search ............................. 175/20, 5, 7, 9, 175/10, 58; 166/336, 264, 338

(56) References Cited

U.S. PATENT DOCUMENTS

| 2,176,477 | A | * | 10/1939 | Varney et al. ................. 175/6 |
| 3,313,345 | A | * | 4/1967 | Fischer ........................ 166/355 |
| 3,412,814 | A | | 11/1968 | Rosfelder |
| 3,438,452 | A | * | 4/1969 | Bernard et al. ................ 175/6 |
| 3,561,547 | A | * | 2/1971 | Pullos ........................... 175/6 |
| 3,741,320 | A | | 6/1973 | Hilfing |
| 5,069,488 | A | * | 12/1991 | Freyer et al. ............... 285/302 |
| 6,394,192 | B1 | * | 5/2002 | Frazer ......................... 175/58 |

FOREIGN PATENT DOCUMENTS

| WO | 9909294 | 2/1999 |
| WO | 9910620 | 3/1999 |

* cited by examiner

Primary Examiner—Kenneth Thompson
(74) Attorney, Agent, or Firm—Ostrolenk, Faber, Gerb & Soffen, LLP

(57) ABSTRACT

The invention concerns a device for driving into the marine subsurface, in particular at great depths exceeding a thousand meters, a tubular tool for soil sampling or for measuring said soil characteristics. The invention is characterized in that the tubular tool (1) to be driven into the marine subsurface is secured to a base plate for positioning on the sea floor, and the device comprises at least a fluidic actuator (16), capable of being controlled from the surface, which is fixed to said base plate comprising a piston (4) moving in a cylindrical annular chamber (3) with an axis oriented parallel to the axis (y'y) of the tool (1) penetration, driving in the tool (1) depending on the discharge of intake of the fluid which is produced in said chamber (3), said piston (4) being subjected to the hydrostatic pressure prevailing at the depth where the device has been lowered by being in communication with the marine environment by its side external to said chamber (3).

17 Claims, 3 Drawing Sheets

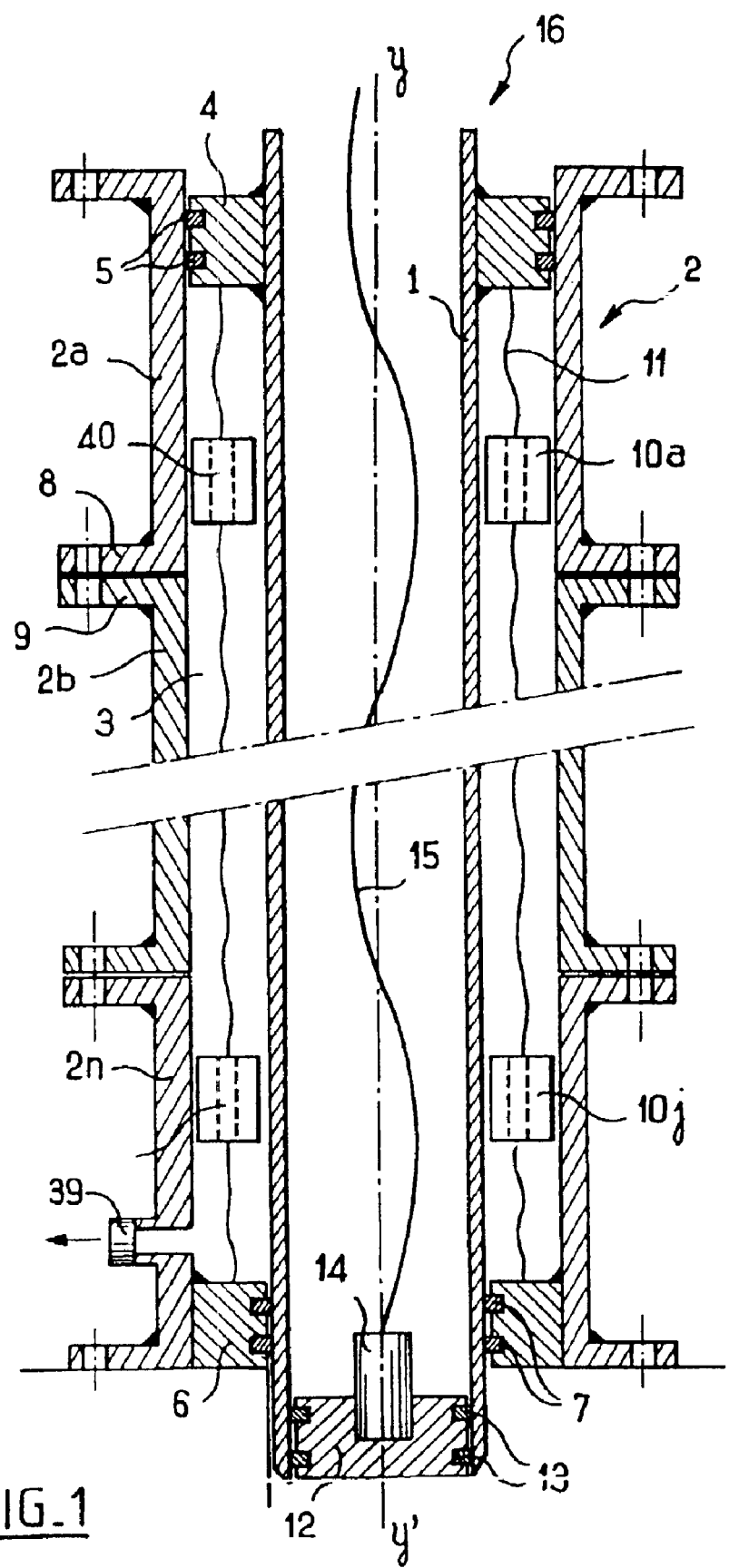
FIG_1

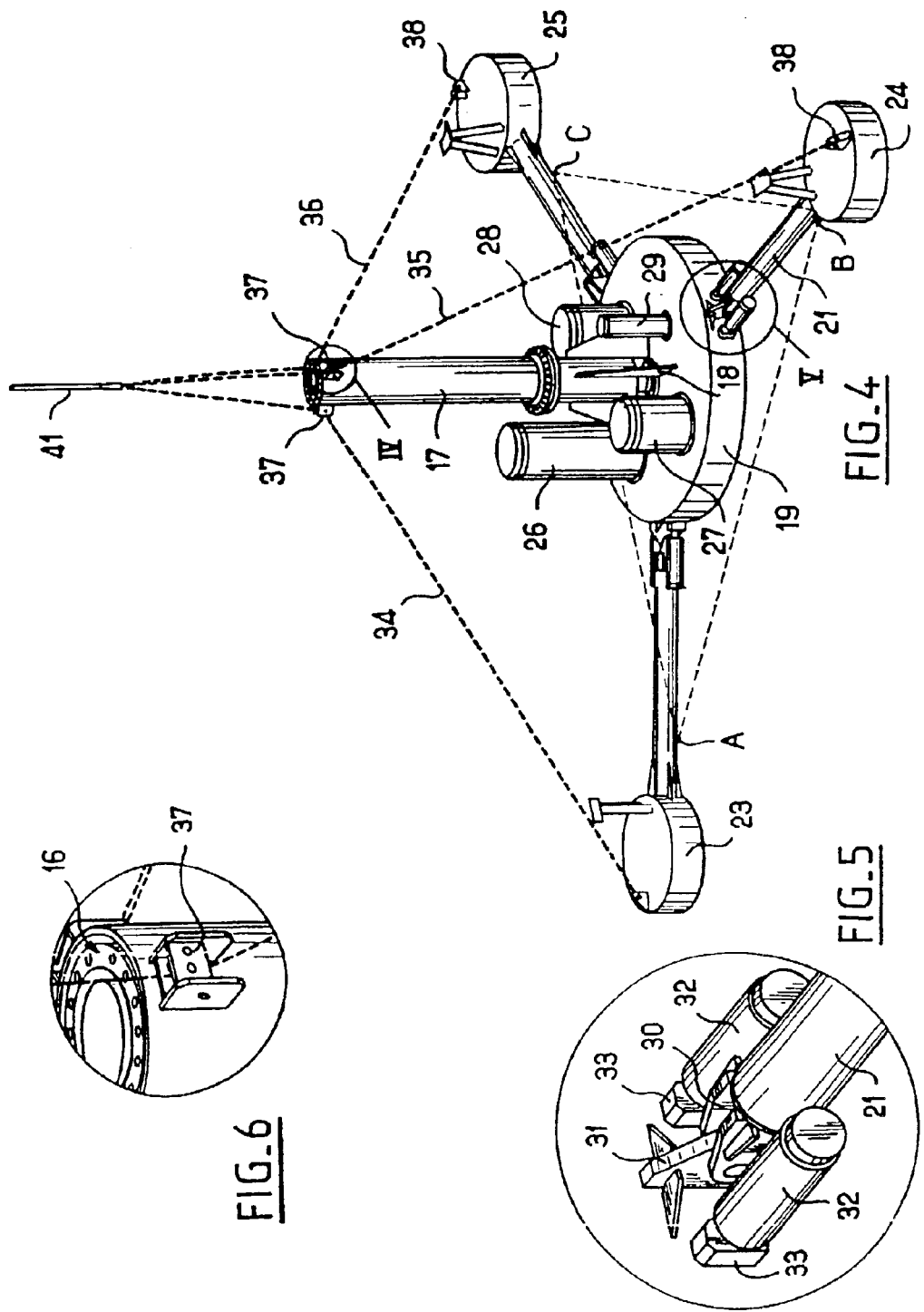

METHOD AND DEVICE FOR DRIVING INTO THE MARINE SUBSURFACE AT GREAT DEPTHS, A TUBULAR TOOL FOR SOIL SAMPLING OR FOR MEASURING SOIL CHARACTERISTICS

This invention concerns a method and a device for driving into the marine subsurface, in particular at great depths exceeding a thousand meters, a tubular tool for soil sampling or for measuring said soil characteristics.

When soil sampling of the marine subsurface or measurements of said soil characteristics must be performed at depths exceeding a thousand meters, major implementation problems come up. At such great depths it is no longer possible to use divers and the use of robots or of submarines specialized in this technology is extremely costly.

For soil sampling, there are various techniques involving samplers launched from the surface from ships or work barges. Although interesting, such techniques are not fully satisfactory in that it is extremely difficult to control and operate with any precision the penetration of the sampler in the marine soil, and particularly the precise location and penetration angle of the sampler. Since the penetration of the sampler in this technique comes essentially from the kinetic inertia acquired during the controlled fall of said sampler, this technique is not suitable whenever the marine subsurface soils present a weak cohesiveness, the subsurface being then deeply altered by the impact itself. Besides, the quality of the sample removed is mediocre since it is impossible to control the penetration speed of the sampler into the subsurface and since this speed obviously decreases as the penetration proceeds.

To address these difficulties inherent to launched samplers, other techniques were developed, particularly ramming techniques using hydraulic, pneumatic or electric engines, that will drive into the marine subsurface a sampler or a measuring probe previously lowered at the desired location. Not only are these solutions very costly and complex, necessitating in particular the prior setup, at the chosen location on the marine subsurface, of a system enabling the guiding and the orientation of the measuring probe or the sampler, but their results have proven quite disappointing.

According to this invention, a device for driving into the marine subsurface, in particular at great depths exceeding a thousand meters, a tubular tool for soil sampling or for measuring said soil characteristics, is characterized in that this tubular tool to be driven into the marine subsurface is secured to a positioning base plate on the ocean floor, said device comprising at least one fluidic jack that can be controlled from the surface and is fastened to said base plate comprising a piston moving inside a cylindrical annular chamber of which the axis is parallel to the tool penetration axis, the tool being driven in depending on the fluid discharge or intake occurring in said chamber, said piston being subjected to the hydrostatic pressure prevailing at the depth where the device was lowered by being in communication with the marine environment by its outer side to said chamber.

It becomes clear therefore that it is the force of the hydrostatic pressure prevailing at the depth level of the marine subsurface where the work is to be done that will allow the penetration of the soil sampler or measuring probe. This force can be considerable and will be precisely known since it is a function of the depth at which the work is to be performed (i.e. of the hydrostatic pressure prevailing on the marine subsurface) and of the surface of the piston face subjected to this pressure. Moreover, the penetration motion being a direct function of the displacement of the piston in the jack chamber, i.e. of the fluid volume discharged from the chamber, to control this motion simply requires controlling the corresponding discharge.

According to another advantageous characteristic of this device, the tubular tool is constituted at least partly by said piston of the fluidic jack. Advantageously, near the upper portion of the jack, is set an annular piston that slides in a watertight way in said chamber that is integral with the outer wall of the part facing the tool, while at the jack base is an annular piston integral with the inner wall of the outer tube of the jack inside which the outer wall of the part facing the tool slides in a watertight way. Thus, the tubular tool can be simply shaped essentially like a piston rod that slides inside the outer cylindrical chamber of the jack and is fastened in its upper part, by welding for instance, to the piston to be subjected to the hydrostatic pressure of the marine environment.

According to a preferred embodiment, the device comprises at least one hydraulic pump mounted on said base plate to carry out the intake or discharge of the fluid in said chamber. This, by controlling from the surface the discharge or intake flow of the jack chamber, it becomes possible to control precisely the penetration or retrieval motions of the sampler or the measuring probe that forms the piston of the jack. It is thus possible to obtain much improved sample qualities as well as an unprecedented precision of the recorded measurements.

Preferably, said base plate is integral with a legstand that ensures the good positioning and orientation of the device on the marine subsurface. This legstand can be hinged, or telescopic or collapsible or any other type of legstand that can be hydraulically controlled for instance, of the tripod type for instance, capable of moving and in particular of orienting itself vis-à-vis the vertical direction.

To ensure a good holding behavior of the legstand on the marine subsurface, said legstand is advantageously designed with suction feet, with at least one hydraulic pump provided on the base plate to perform this suction. When such a technique is used, it becomes possible to create from a light structure the reaction force suitable to generate a substantial driving force of the tool into the marine subsurface without having to considerably ballast the base plate.

When this device is used as a sampler, the tubular tool will advantageously be designed with, at least at its lower end, a shutter such as a gate valve. It becomes thus possible to pull up the soil sample without damaging it.

This invention relates also to a method for driving into the marine subsurface, in particular at great depths exceeding a thousand meters, a tubular tool for soil sampling or for measuring said soil characteristics operated from the surface via an on-board instrumentation provided on said tool, the driving motion into the marine subsurface or its retrieval motion being controlled by the discharge of the fluid contained in the chamber or by the intake of the fluid into that chamber.

Other characteristics, objects and advantages of this invention will appear more clearly from the following description in reference to the accompanying drawings that illustrate an example of a possible embodiment of this invention.

In these drawings:

FIG. 1 is a lengthwise sectional view of a driving tool according to this invention;

FIG. 4 is a perspective view of the base plate of FIG. 2, with the legstand in its extended position;

FIG. 5 is an enlarged view of the detail circled in V in FIG. 4;

FIG. 6 is an enlarged view of the detail circled in VI in FIG. 4.

Figures 2, 3:
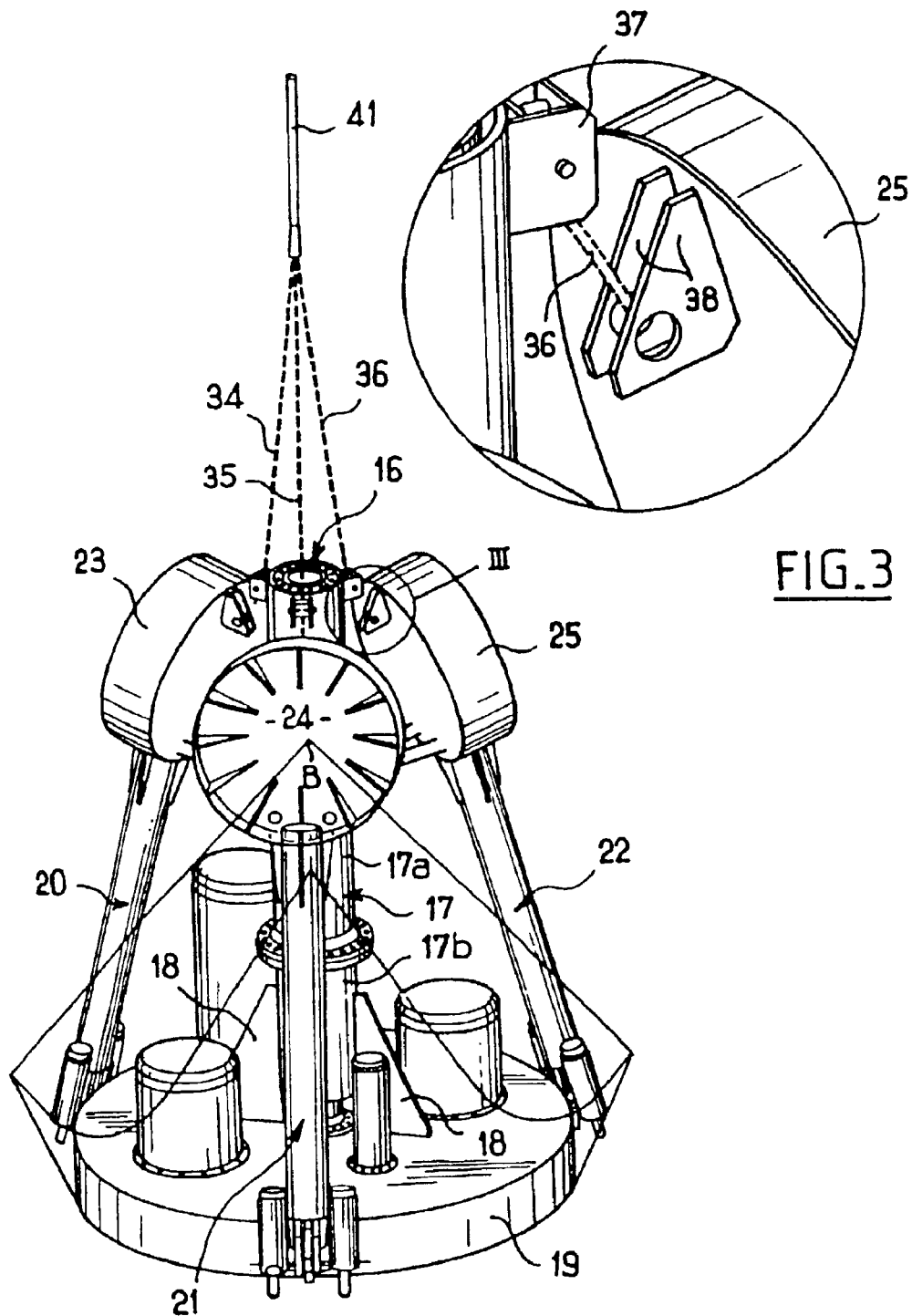
FIG. 2 is a diagram on a smaller scale showing in a folded position and in perspective a base plate designed for the tool of this invention.
FIG. 3 is an enlarged view of the detail circled in III in FIG. 2.

We will refer firstly to FIG. 1 in which has been shown a driving tool according to the invention.

Referring to FIG. 1, the driving tool is essentially tubular with an inner tube 1, an outer tube 2, between which is formed an annular chamber 3. The upper portion of the inner tube 1 is integral, by welding for instance, with an annular piston 4 that slides against the inner wall of the outer tube 2, in a watertight way ensured by means, for instance, of sealing rings 5. The outer wall of the lower part of said inner tube 1 slides tightly against an annular piston 6 integral with the outer tube 2, by welding for instance. To provide a tight seal, the piston 6 may be provided, for instance, with sealing rings 7.

In order to facilitate the assembling and to provide whatever adjustment of the length of the driving tool may be needed, the inner tube 1 is advantageously implemented in several portions screwed to one another end to end; they can be made of steel, for instance. Likewise, the outer tube 2 is advantageously implemented in several portions referenced in 2a, 2b, ..., 2n. In the illustrated example, the ends of the various portions 2a, 2b, ..., 2n, are assembled end to end by means of sleeves or joint flanges such as 8, 9 that hold together the two portions 2a, 2b, thus improving the overall rigidity of the assembly.

To improve the resistance to pressure of the chamber 3, the device comprises advantageously annular spacing elements such as 10a, ..., 10j in FIG. 1. These spacers may be distributed along the cables 11, and will be capable of sliding on the cables when the inner tube 1 slides inside the outer tube 2 and the piston 4 moves closer to the piston 6. Said spacers are also designed with holes 40 to ensure the free passage of the fluid in the chamber 3 on either side.

A piston 12 seals the lower end of the tube 1 by means of sealing rings 13. On the piston 12 is outlined an instrumentation 14 fastened to the end of a feeder cable 15 that also performs the positioning of the instrumentation 14.

The driving device thus described in FIG. 1 and referenced as a whole in 16 is designed to be mounted on a positioning base plate on the marine subsurface that will be now described more particularly in reference to FIG. 2 to 6.

As appears more clearly in FIG. 2, the driving device 16 is mounted locked inside a tube 17 of which the inner diameter is slightly superior to the outer diameter of the flanges 8, 9 of FIG. 1. Said tube 17 is long enough to provide a good behavior of the driving tool 16 within it. It can be shorter, particularly if the driving device is very long. This locking can be implemented by any means, e.g. by a bayonet locking system, between the outer tube 2 of the driving device and the inner surface of the tube 17, or else by a cam system that will enable the wedging of the tube 2 in the tube 17.

The tube 17 can consist of several portions, e.g. of two portions as shown in 17a, 17b held together by flanges like the portions 2 of the outer tube of the driving device 16. The lower portion 17b is securely fastened, by means of brackets 18 for instance, to a base plate 19, made of steel for example. On this base plate 19 are hinged the three legs 20, 21, 22 of a tripod legstand with three feet 23, 24, 25.

On the base plate 19 are also set three hydraulic pumps 26, 27, 28 respectively. Their role and use will be described thereafter. 29 represents a telemetry and remote control module enabling to locate and guide from the surface the perfect positioning on the marine subsurface of the base plate with its legstand.

In the embodiment illustrated in FIG. 2 to 6, the three legs 20, 21, 22 of the tripod legstand are hinged on the base plate 19, as shown more clearly in FIG. 5 where the leg 21 of the tripod is shown hinged on its base plate by a fork joint 30 on a fitting 31 welded on the periphery of the base plate 19. The leg 21 also comprises on each side pressure spring latches 32 that, by leaning on the pads 33 welded to the periphery of the base plate 19, come to lock, in the spread-out position shown in FIG. 4, the legs of the legstand of the base plate once they have been extended. In the illustrated embodiment, the extension of the legs of the legstand is obtained by letting the three cables 34, 35 and 36 run and go through unwinding-knobs 37 fastened near the upper part of the tube 17, said cables being fastened by their upper end to another cable 41 that can be pulled up or lowered from the surface.

FIG. 4 shows in A, B, and C the vertex of a triangle formed by a net fastened under the legs 23, 24, 25 of which the three angles in the startup position of the base plate illustrated in FIG. 2 are gathered, like the three feet 23, 24, 25, against the upper extremity of the tube 17. This net provides an improved stabilization of the legstand when it is put down on the ocean floor.

FIGS. 2 and 3 show the position of the cables 34, 35, 36 before the extension of the legs of the legstand, and how the feet 23, 24, 25 are held against the tube 17 by a fork joint 38 welded on the upper face of each foot.

The implementation of the invention will be now described.

With the driving device 16 inside the tube 17 of the base plate, said base plate being in the folded position of FIG. 2, the whole device is lowered on the ocean floor at the location chosen for the sampling or the measurement.

When the plate 19 lands on the marine subsurface, the legs of the legstand automatically spread out because of their weight to the position illustrated in FIG. 5, with the stabilization net stretched between the feet.

The pump 27 is then actuated, said pump communicating by a tubing [not represented] with the inner hollow face forming cup of each foot 23, 24, 25, to create a vacuum in the volume of each foot. This suction, according to a well-known principle, enables to apply the base plate of the device on the ocean floor with a considerable strength that depends on the volume created under each foot. The volume of the feet is chosen so as to provide an application force on the ocean floor at least equal to the driving force of the drilling tool into the ocean floor.

Once this device is set on the marine subsurface, it becomes possible to operate the drilling device forming fluidic jack. All that needs to be done then is to start the hydraulic pump 26 which is connected to the volume of the chamber 3 through the communication 39 of FIG. 1. The pump 26 is of the reversible type, enabling the intake or the discharge of the fluid in the chamber 3. To drive the tool 1 into the soil, the fluid contained in the chamber 3 is sucked in by means of the pump 26. Said fluid will usually be ocean water that the pump will discharge in the marine environment. The hydraulic pressure prevailing above the piston 4 thus generates the sliding of said piston 4 and of the tube 1 integral with it, driving it into the marine subsurface against the suction force of the feet 23, 24, 25 and the weight of the base plate.

This technique makes it possible, by using the on-board instrumentation 14 while controlling the flow of the hydraulic pump 26, to obtain a perfectly constant penetration speed, 2 centimeters per second (2 cm/s) for instance with a margin of more or less half a centimeter per second [½ cm/s]. A precise and reliable control of the penetration speed can thus be achieved and continuously watched from the surface.

The tool 1 can be, as illustrated, a sampling tube. In this case, as the soil is penetrated by the tube 1 that slides parallel to the axis yy' of the device, the piston 12 goes up together with the instrumentation 14, process that can be controlled in particular by the roll back of the cable 15. In this case, too, it is advantageous to provide the lower end of the tube 1 with a shutter such as for instance a gate valve [not represented] that will be open during the penetration and sealed when the tool is lifted. To move the tool upward only entails reversing the operation of the pump 26 to fill up again the chamber 3 with the fluid, thus moving the piston 4 upward against the hydraulic pressure of the environment by pumping through the connection 39 the ocean water of the environment, said pump then providing the needed pressure differential.

The recovery of the whole device will be performed simply by reeling in the cable 41, after reversing the suction in the feet 23, 24, 25 to release them from the marine subsurface. The feet are lifted first to go back to the position illustrated in FIG. 2.

The tool 1 can also be constituted by a measuring probe, for instance to gather electric data that will provide information about the quality of the soils.

In a practical embodiment, the diameter of the inner tube 1 can be three inches (7.62 cm) and the inner diameter of the outer tube 2 six, seven or eight inches (15.24, 17.78, 20.32 cm). Under such conditions, the hydraulic pressure acting on the piston 4 varies with the different depths, according to the calculations performed, from 13 tons at a 1,000-meter depth with an 6-inch outer tube of, or 27 tons for a 2,000-meter depth with an 8-inch outer tube and 27 tons for a 2,000-meter depth with a 6-inch outer tube up to 55 tons for a 2,000-meter depth and a 8-inch outer tube. The values indicated are only approximate and depend on the frictional forces.

It is thus possible to determine precisely the most appropriate tool, depending on the work to be done and the soils encountered.

With a device according to this invention, it becomes possible to work at great depths, up to 3,000 meters, with a simple technology and the use of light structures, since this device operation only requires known organs such as hydraulic high-pressure pumps that can be fed for instance by a standard power cable allowing to convey a power of six kilowatts (6 KW) to the depth of the work.

The driving tools will be of variable length depending on the work to be performed, e.g. 10 to 30 meters by means of multiple 5-meter units.

Although this description relates to a tripod with hinged legs, it is of course possible to provide other types of legstands, for instance a tripod or quadripod with collapsible legs of which the length and/or the orientation can be controlled from the surface by means of an auxiliary hydraulic pump such as the pump 28.

What is claimed is:

1. A device for at least one of soil sampling and measuring soil characteristics of soil below a marine subsurface, the device comprising:
    a base plate for positioning the device within a marine environment on the marine subsurface;
    a fluidic jack secured to the base plate, the fluidic jack including an outer tube, an inner tubular tool within the outer tube forming an annular chamber between the tubular tool and the outer tube, the annular chamber being sealed, and a piston attached to the tubular tool within the annular chamber, the piston being configured to seal the annular chamber from the marine environment and to slidably move together with the tubular tool within the annular chamber, the piston having an outer surface away from the annular chamber and adapted for communication with the marine environment for exposing the piston to a hydrostatic pressure of the marine environment; and
    a controllable hydraulic pump in fluid communication with the annular chamber of the fluidic jack which is sealed by the piston, the hydraulic pump being operable to selectively pump a fluid into and out of the annular chamber for slidably moving the piston together with the tubular tool respectively upwardly or downwardly within the annular chamber in a controlled manner.

2. The device according to claim 1, wherein the tubular tool and the piston form a single integral unit.

3. The device according to claim 1, wherein the outer tube includes a plurality of outer tube portions fastened end to end.

4. The device according to claim 1, wherein the tubular tool includes, at least in part, a plurality of inner tube portions fastened end to end.

5. The device according to claim 1, further comprising a second annular piston arranged in the annular chamber and formed integrally with the outer tube, the second annular piston permitting the tubular tool to slide within the annular chamber in a waterproof manner.

6. The device according to claim 1, wherein the tubular tool includes a base and an instrumentation arranged at the base of the tubular tool for control and registering of the measurements performed by the tool.

7. The device according to claim 1, wherein the hydraulic pump is mounted on the base plate and the fluid includes ocean water exchanged with the marine environment.

8. The device according to claim 1, wherein the controllable hydraulic pump is in fluid communication only with the annular chamber of the fluidic jack in order to pump fluid only into and out of the annular chamber.

9. The device according to claim 1, wherein the hydraulic pump is in fluid communication with the marine environment external to the outer tube.

10. The device according to claim 1, wherein the base plate includes a legstand for positioning and orienting the device on the marine subsurface.

11. The device according to claim 10, wherein the legstand includes a plurality of suction feet and the base plate further includes at least one base plate hydraulic pump to form a vacuum at each of the suction feet so that the device is forcefully positioned on the marine subsurface.

12. The device according to claim 1, wherein the tubular tool is a sampling tool and includes a sealing organ.

13. The device according to claim 12, wherein the sealing organ is a gate valve.

14. Method for driving into the marine subsurface a tubular tool for at least one of soil sampling and for measuring soil characteristics, the method comprising:
    submerging a device for at least one of soil sampling and measuring soil characteristics of soil below a marine subsurface, the device comprising:
    a base plate for positioning the device within a marine environment on the marine subsurface;
    a fluidic jack secured to the base plate, the fluidic jack including an outer tube, an inner tubular tool within the outer tube forming an annular chamber between the tubular tool and the outer tube, the annular chamber being sealed, and a piston attached to the tubular tool within the annular chamber, the piston being configured to seal the annular chamber from the marine environment and to slidably move together with the tubular tool within the annular chamber, the piston having an outer surface away from the annular chamber and adapted for communication with the marine environment for exposing the piston to a hydrostatic pressure of the marine environment; and a controllable hydraulic pump in fluid communication with the annular chamber of the fluidic jack which is sealed by the piston, the hydraulic pump being operable to selectively pump a fluid into and out of the annular chamber for slidably moving the piston together with the tubular tool respectively upwardly or downwardly within the annular chamber in a controlled manner;

the method further comprising controlling, using the hydraulic pump, the pumping of the fluid into or out of the annular chamber of the fluidic jack of the device for slidably moving the piston and the tubular tool within the annular chamber downwardly into the marine subsurface and then upwardly for the at least one of soil sampling and measuring soil characteristics below the marine subsurface.

15. The method of claim 14, wherein the pumping of the fluid out of the annular chamber along with the exposing of the piston to the hydrostatic pressure causing the piston and the tubular tool to slide downwardly within the outer tube of the fluidic jack in the controlled manner, the pumping of the fluid into the annular chamber causing the piston and the tubular tool to slide upwardly within the annular chamber of the fluidic jack in the controlled manner.

16. The method of claim 14, wherein the fluid is seawater.

17. A device for at least one of soil sampling and measuring soil characteristics of soil below a marine subsurface, the device comprising:

a base plate for positioning the device within a marine environment on the marine subsurface;

a fluidic jack secured to the base plate, the fluidic jack including an outer tube, an inner tubular tool within the outer tube forming an annular chamber between the tubular tool and the outer tube, the annular chamber being sealed, and a piston attached to the tubular tool within the annular chamber, the piston being configured to seal the annular chamber from the marine environment and to slidably move together with the tubular tool within the annular chamber, the piston having an outer surface away from the annular chamber and adapted for communication with the marine environment for exposing the piston to a hydrostatic pressure of the marine environment; and a controllable hydraulic pump in fluid communication with the annular chamber of the fluidic jack which is sealed by the piston, the hydraulic pump being operable to selectively pump a fluid into or out of the annular chamber for slidably moving the piston together with the tubular tool respectively upwardly or downwardly within the annular chamber in a controlled manner;

wherein the fluidic jack further includes a plurality of spacing rings slidably arranged within the annular chamber between the inner tubular tool and the outer tube, and guiding cables cooperating with the spacing rings for guiding the sliding of the spacing rings, each of the spacing rings being shaped to form at least one hole therethrough for permitting the fluid to pass.

* * * * *